US009827586B2

(12) United States Patent
Evans et al.

(10) Patent No.: US 9,827,586 B2
(45) Date of Patent: Nov. 28, 2017

(54) COATED MICROBUBBLES

(71) Applicant: University of Leeds, Leeds (GB)

(72) Inventors: Stephen Evans, Leeds (GB); Sally Peyman, Leeds (GB); Jonathan Blockley, Leeds (GB)

(73) Assignee: University of Leeds (GB)

(*) Notice: Subject to any disclaimer, the term of this patent is extended or adjusted under 35 U.S.C. 154(b) by 218 days.

(21) Appl. No.: 14/568,677

(22) PCT Filed: Jul. 3, 2013

(86) PCT No.: PCT/GB2013/051764
§ 371 (c)(1),
(2) Date: Dec. 12, 2014

(87) PCT Pub. No.: WO2014/006404
PCT Pub. Date: Jan. 9, 2014

(65) Prior Publication Data
US 2015/0099055 A1     Apr. 9, 2015

(30) Foreign Application Priority Data

Jul. 3, 2012  (GB) .................................. 1211783.4

(51) Int. Cl.
*B01J 12/00* (2006.01)
*B05C 3/02* (2006.01)
(Continued)

(52) U.S. Cl.
CPC .............. *B05C 3/02* (2013.01); *A61K 49/223* (2013.01); *B01J 13/04* (2013.01); *B01J 13/22* (2013.01); *B05D 1/18* (2013.01)

(58) Field of Classification Search
CPC .................................. B05C 3/02; B01J 13/02
See application file for complete search history.

(56) References Cited

U.S. PATENT DOCUMENTS

| 2005/0121604 A1 | 6/2005 | Meuth |
| 2005/0248696 A1* | 11/2005 | Miller ...................... B01J 13/10 349/86 |
| 2011/0104777 A1 | 5/2011 | Marquez |

FOREIGN PATENT DOCUMENTS

| WO | WO9917119 A1 | 4/1999 |
| WO | 2007028984 | 3/2007 |

(Continued)

OTHER PUBLICATIONS

Ryan D Sochol et al: "Continuous flow layer-by-layer microbead functionalization via a micropost array railing system", 2011 16th International Solid-State Sensors, Actuators and Microsystems Conference (Transducers 2011): Beijing, China, Jun. 5-9, 2011, IEEE, Piscataway, NJ, Jun. 5, 2011 (Jun. 5, 2011), pp. 1761-1764.

(Continued)

*Primary Examiner* — Robert Vetere
(74) *Attorney, Agent, or Firm* — Dickinson Wright PLLC

(57) ABSTRACT

The present invention relates to methods and apparatus to provide coated microbubbles, particularly but not exclusively microbubbles at least partially coated with a component, for example a clinically active component. Systems of the present invention use electromagnetic fields to move microbubbles between streams of liquids in order to perform coating or washing steps.

5 Claims, 1 Drawing Sheet

(51) Int. Cl.
*B01J 13/04* (2006.01)
*B01J 13/22* (2006.01)
*A61K 49/22* (2006.01)
*B05D 1/18* (2006.01)

(56) References Cited

FOREIGN PATENT DOCUMENTS

WO     WO2009020229 A2    3/2009
WO     WO 2009029229 A2 *    3/2009   ............ B01F 3/0807

OTHER PUBLICATIONS

PCT International Search Report for PCT/GB2013/051764, dated Feb. 2, 2014.
Chiatanya Kantak et al.: "A 'microfluiclic pinball' for on-chip generation of Layer-by-Layer polyelectrolyte microcapsules", Lab on a Chip. vol. 11, No. 6, Jan. 1, 2011 (Jan. 1, 2011), p. 1030.

* cited by examiner

COATED MICROBUBBLES

CROSS-REFERENCE TO RELATED APPLICATIONS

The present application is a 35 U.S.C. Section 371 national stage filing of International Patent Application No. PCT/GB2013/051764, filed 3 Jul. 2013, and through which priority is claimed to UK application GB 1211783.4, filed 3 Jul. 2012, the disclosures of which are incorporated herein by reference in their entireties.

The present invention relates to the provision of coated microbubbles, specifically but not exclusively microbubbles at least partially coated with a component, for example a clinically active component.

It is known in the prior art that microbubbles, by which is meant bubbles having a diameter of less than 20 μm, preferably less than 15 μm, may be used as ultrasound contrasting agents or as drug delivery vehicles. In brief a microbubble will have a gas core, a shell material surrounding the core and may carry an active. Such microbubbles are typically prepared within a microfluidic device.

The gas core of an ultrasound contrast microbubble determines the 'echogenicity'. When gas bubbles are caught in an ultrasonic frequency field, they compress, oscillate, and reflect a characteristic echo. This echo generates a strong and unique sonogram. Gas cores can be composed of air or nitrogen, or heavy gases like fluorocarbon. Heavy gases are less water-soluble so they are less likely to leak out from the microbubble to impair echogenicity. Therefore, microbubbles with heavy gas cores are likely to last longer in circulation.

The shell material affects microbubble mechanical elasticity. The more elastic the material, the more acoustic energy it can withstand before bursting. Currently, microbubble shell materials may be composed of albumin, galactose, lipid, or polymers.

It is possible to control the movement of a microbubble using sonography. This property also makes microbubbles potentially very useful in the delivery of actives to a site of use.

It is known that actives can be provided either within a microbubble or on a microbubble. For example chemotherapeutic agents can be bound to a bubble for targeted release within a body.

The provision of monodisperse populations of microbubbles is beneficial because the interaction with ultrasound radiation can more efficient. Moreover, the capacity of radiation to cause motion in microbubbles is likely to be more effective with a monodisperse population and a particular frequency. The disruption (i.e. collapse) of the bubbles is improved when using a single frequency.

A further advantage with monodisperse populations is that a larger amount of bubbles from a population can access a particular site of use, for example, through capillaries in the human body, or entering tissue.

Monodisperse in this context means a population of microbubbles in which a high proportion of generated microbubbles have a diameter which is within a single standard deviation of the mean and wherein the standard deviation is small when compared to the mean.

Another factor is to be able to generate microbubble populations quickly enough so that an effective amount can be generated in a (clinically, for example diagnostically or therapeutically) sensible time period. The generation of monodisperse populations and fast generation are typically in competition.

In the prior art ways have been postulated to provide microbubbles which are at least partially coated with an active. It is an objection of this invention to provide apparatus which is more efficient in coating microbubbles.

Accordingly, in a first aspect of the invention, there is provided apparatus, e.g. microfluidic apparatus, for coating microbubbles with a coating, the apparatus comprising an input for a microbubble stream, an input for a coating stream and a contact chamber adapted to allow streams entering through the inputs to establish separate laminar flows therein, and means to cause microbubbles in a microbubble stream within the contact chamber to enter, and preferably then exit, a coating stream within the contact chamber across a flow boundary established therein.

A second aspect of the invention provides a method of coating a microbubble, the method comprising providing separate laminar flows of a coating stream and a microbubble stream and causing microbubbles within the microbubble stream to cross the flow boundary between the streams into the coating stream to become at least partially coated with the coating and then causing the at least partially coated bubbles to cross the flow boundary into the microbubble stream.

In order that the invention may be more fully understood, preferred embodiments in accordance with the invention will now be described, by way of example only, and with reference to the accompanying drawings in which.

Figure 1:
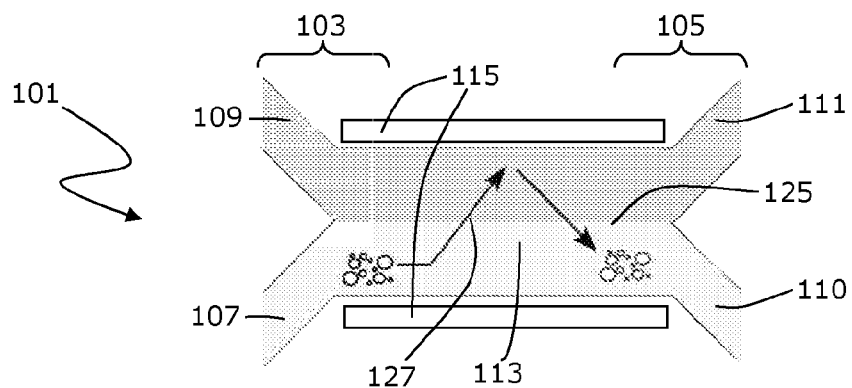
FIG. 1 is a cross-sectional schematic view of an apparatus for coating microbubbles with a coating according to the present invention shown in use.

Referring firstly to FIG. 1, there is provided an apparatus for coating microbubbles with a coating (which is part of a microfluidic device), indicated generally at 101, comprises an upstream end 103 and a downstream end 105.

At the upstream end 103 of the apparatus 101, there is a first input for a microbubble stream 107 and a second input 109 for a coating stream.

At the downstream end 105 of the apparatus 101, there is a first output 110 for the microbubble stream and a second output 111 for the coating stream.

Between the inputs 107, 109 and the outputs 110, 111, there is a contact chamber 113. Adjacent the contact chamber 113, there is provided an electric field generator 115 to generate an electric filed across the contact chamber 113.

In use, a microbubble stream, which may be provided by any means known in the art, is provided to the first input 107 and a coating stream is provided to the second input 109. The microbubble stream flows through the first input 107, the contact chamber 113, and the first output 110. The coating stream flows through the second input 109, the contact chamber 113 and the second output 111.

Within the contact chamber 113 both the microbubble stream and the coating stream are in laminar flow. The laminar flow of both streams establishes a flow boundary 125 within the contact chamber 113. Across the flow boundary 125 there is essentially no bulk flow between the microbubble stream and the coating stream. However, diffusion between the microbubble stream and the coating stream (and vice versa) may occur across the flow boundary 125.

Thus, absent an applied electric field, the microbubble stream and the coating stream come into contact with each other within the contact chamber 113 with essentially no mixing therebetween.

In use, an electric field is applied across the contact chamber 113 by the electric field generator 115. The electric field may be static or varied through time. The electric field is applied such that the microbubbles cross the flow boundary 125 and enter the coating stream towards the upstream end 103 of the apparatus 101 and cross back across the flow boundary 125 and re-enter the microbubble stream towards the downstream end 105 of the apparatus 101. A typical flow path 127 is shown in FIG. 1.

Whilst the microbubbles are within the coating stream, the microbubbles become at least partially coated with the coating. The microbubbles exit the apparatus 101 within the microbubble stream via the first output 110. The at least partially coated microbubbles may then be collected for later use or used immediately.

Figure 2:
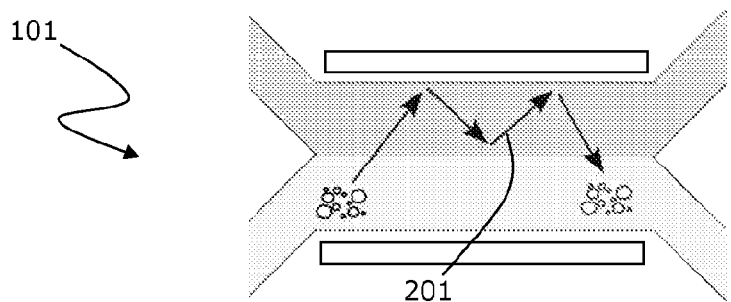
FIG. 2 is a cross-sectional schematic view of the apparatus of FIG. 1 also shown in use.

FIG. 2 shows an alternative method of use of the apparatus 101. An electric field is applied by the electric field generator 115 to cause the microbubles to remain within the coating stream for a prolonged period of time. A typical flow path 201 is shown in FIG. 2.

Figure 3:
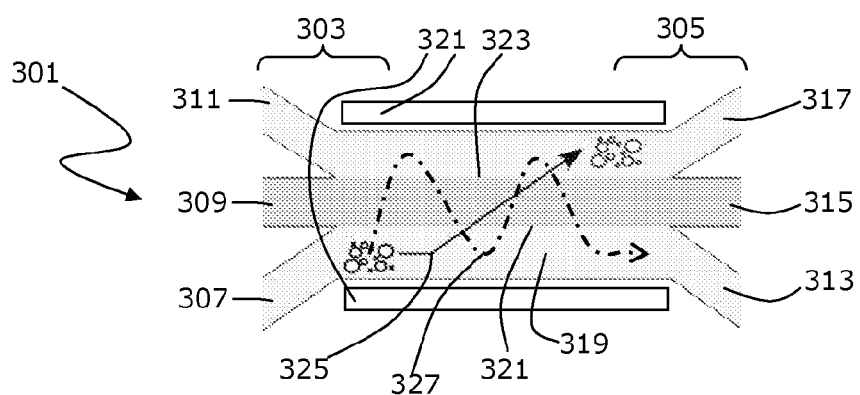
FIG. 3 is a cross-sectional schematic view of an alternative apparatus for coating microbubbles with a coating according to the present invention shown in use.

Referring to FIG. 3, an alternative apparatus for coating microbubbles with a coating (which is part of a microfluidic device), indicated generally at 301, comprises an upstream end 303 and a downstream end 305.

At the upstream end 303, there is a first input 307 for a microbubble stream, a second input 309 for a coating stream and a third input 311 for a washing stream. At the downstream end 305, there is a first output 313 for the microbubble stream, a second output 315 for the coating stream and a third output 317 for the washing stream.

Between the inputs 307, 309, 311 and the outputs, there is a contact chamber 319. Adjacent the contact chamber, there is also an electric field generator 321 to apply an electric filed across the contact chamber 319.

In use, a microbubble stream (which may be provided by any means known in the art) is provided to the first input 307, a coating stream is provided to the second input 309 and a washing stream is provided to the third input 311.

The microbubble stream flows thorough the first input 307, the contact chamber 319, and the first output 313. The coating stream flows through the second input 309, the contact chamber 319, and the second output 315. Similarly, the washing stream flows through the third input 311 the contact chamber 319, and the third output 317.

Within the contact chamber 113 both the microbubble stream, the coating stream and the washing stream are in laminar flow. This laminar flow establishes a first flow boundary 321 within the contact chamber 319 between the microbubble stream and the coating stream, and a second flow boundary 323 also within the contact chamber 319 between the coating stream and the washing stream. These flow boundaries 403, 405 have similar properties to the flow boundary 125 described above, that is—essentially no mixing takes place across the flow boundaries 321, 323.

In use, an electric field is applied across the contact chamber 319 by the electric field generator 321. The electric field may be applied such that the microbubbles cross the first flow boundary 403 and enter the coating stream. Whilst the microbubbles are within the coating stream, they become at least partially coated with the coating. The microbubble may then, due to the applied electric field, cross the second flow boundary 405 and enter the washing stream. Whilst the microbubbles are within the washing stream, any excess coating may be at least partially removed. Such a flow path 325 is shown in FIG. 3.

Figure 4:
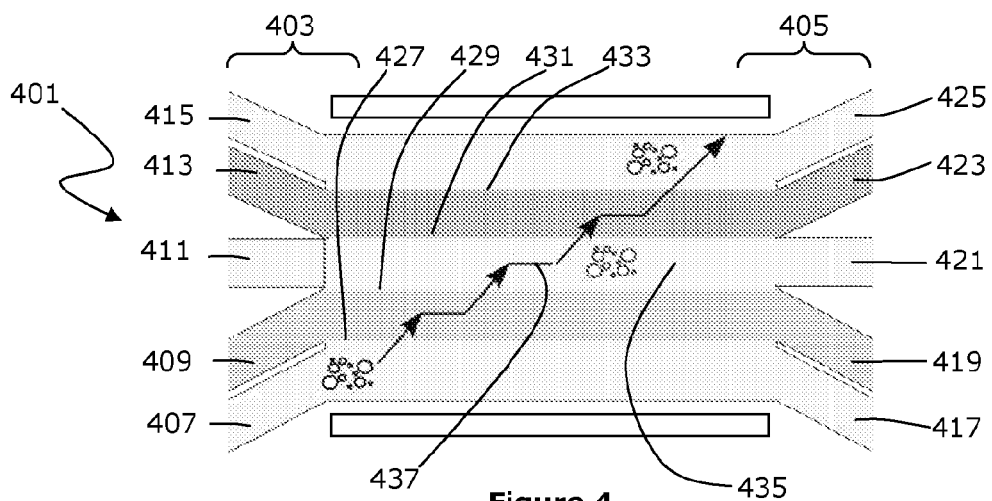
FIG. 4 is an alternative embodiment of apparatus according to the invention shown in use.

Optional further application of electric fields by the electric field generator 321 causes the microbubbles to cross the flow boundaries 403, 405 as many times as necessary to provide microbubbles with the desired coatings. Such a typical flow path 327 is also shown in FIG. 4.

The microbubbles may be directed to exit via any of the outputs 313, 315, 317, however, it is typically preferred for the microbubbles to exit via the first output 313 in the microbubble stream or via the third output 317 in the washing stream.

The above described apparatus 101, 301 and methods are advantageous as microbubbles may be readily removed from excess coating agents. Further, the apparatus and method may be used to prepare microbubbles with novel coatings.

The microbubbles may be used as ultrasound contrast agents or to deliver a payload to a targeted site, e.g. a tumour.

It will be appreciated that the invention is not limited to the foregoing description of preferred embodiments and that modifications may be made within the scope of the Claims appended hereto.

For example, the apparatus and methods may be used to coat particles, vesicles, liposomes, etc. The apparatus and methods may be used to wash, instead of coat, microbubbles, etc. Any number of streams serving different functions with flow boundaries therebetween may be provided. An example of an apparatus 401 providing multiple flows is provided in FIG. 4. At the downstream end 403 of the apparatus 401 there are five inputs 407, 409, 411, 413, 415, for a microbubble stream, a first coating stream, a first washing stream, a second coating stream, and a second washing stream, respectively. At the downstream end 405 of the apparatus 401 there are five corresponding outputs 417, 419, 421, 423, 425. In use four flow boundaries 427, 429, 431, 433 are established within the contact chamber 435. An electric field is applied such that microbubbles cross the flow boundaries 427, 429, 431, 433; a typical flow path 437 is shown. Alternatively an electric field may be applied such that the microbubbles spend different amounts of time in any particular stream or such that the microbubbles cross a chosen flow boundary more than once. The electric field may be applied such that the microbubbles exit in any chosen output 417, 419, 421, 423, 425.

In a most preferred embodiment, the microbubbles are lipid coated. The lipid coating provides the microbubbles with a slight negative charge. The application of a positive electric field will draw the lipid coated microbubbles toward that side of the contact chamber and into and/or through the coating stream. Preferably the coating stream comprises an active which coats, e.g. binds to, the lipid coating. In this way, a coated microbubble can be produced. The microbubble coating can comprise a chemotherapeutic agent or other active.

In a preferred embodiment the generated electric field may be an AC field. The frequency of the field will thereby determine the number of passes the microbubbles make into and out of the coating stream. Plural generators may be used along the length of the devices 101, 301, 401.

The various components of the apparatus may be etched on to a chip, for example mechanically or chemically etched. Other methods may be used. Laminar flow nozzles may be used to establish laminar flow within the contact chamber. The laminar flow nozzles may be adjacent the inputs and/or outputs.

The invention claimed is:

1. A method of coating a microbubble, the method comprising providing in a contact chamber separate laminar flows of a coating stream and a microbubble stream and causing, by use of an electrical field, microbubbles within the microbubble stream to cross the flow boundary between the streams into the coating stream to become at least partially coated with the coating.

2. A method according to claim 1, comprising subsequently causing the at least partially coated bubbles to cross the flow boundary into the microbubble stream.

3. A method according to claim 1, comprising subsequently causing the at least partially coated bubbles to cross a flow boundary into a washing stream.

4. A method according to claim 1, comprising bringing the microbubbles into contact with plural coating streams within the contact chamber.

5. A method according to claim 1, comprising providing as the microbubbles lipid-coated microbubbles.

* * * * *